United States Patent [19]
Hawke et al.

[11] Patent Number: 5,641,390
[45] Date of Patent: Jun. 24, 1997

[54] LABELLED SUGARS IMMOBILIZED ON A SOLID SUPPORT

[75] Inventors: David Harry Hawke, Hayward, Calif.; Paul Goulding, Abingdon, United Kingdom

[73] Assignee: Oxford Glycosystems Ltd., Abingdon, United Kingdom

[21] Appl. No.: 545,820

[22] PCT Filed: May 20, 1994

[86] PCT No.: PCT/GB94/01115

§ 371 Date: Apr. 8, 1996

§ 102(e) Date: Apr. 8, 1996

[87] PCT Pub. No.: WO94/28419

PCT Pub. Date: Dec. 8, 1994

[30] Foreign Application Priority Data

May 20, 1993 [GB] United Kingdom ............... 9310468

[51] Int. Cl.⁶ .................................................. G01N 27/26
[52] U.S. Cl. ............................................ 204/450; 536/127
[58] Field of Search .......................... 436/527; 428/146; 536/16.9, 127; 205/421; 204/450, 615, 465, 461, 612; 430/515

[56] References Cited

U.S. PATENT DOCUMENTS

| | | | |
|---|---|---|---|
| 3,666,421 | 5/1972 | Price | 422/57 |
| 3,852,496 | 12/1974 | Weetall et al. | 426/41 |
| 3,917,451 | 11/1975 | Groves et al. | 436/518 |
| 4,052,010 | 10/1977 | Baker et al. | 241/20 |
| 4,372,745 | 2/1983 | Mandle et al. | 436/537 |
| 4,725,557 | 2/1988 | Miyauchi et al. | 436/543 |
| 4,879,247 | 11/1989 | Ohlson | 436/527 |
| 4,975,165 | 12/1990 | Brandley | 204/461 |

FOREIGN PATENT DOCUMENTS

| | | |
|---|---|---|
| 143412 | 6/1985 | European Pat. Off. |
| 282474 | 9/1988 | European Pat. Off. |
| 0 303 406 | 2/1989 | European Pat. Off. |
| 0 328 256 | 8/1989 | European Pat. Off. |
| 268161 | 5/1989 | Germany. |
| 63139249 | 6/1988 | Japan. |
| 64-15657 | 1/1989 | Japan. |
| 91/12520 | 8/1991 | WIPO. |

OTHER PUBLICATIONS

Abstract of JP 64–15657 (Meidensha Elec. MFG.) Jan. 19, 1989.

Abstract of DD 268161 (Drescher et al.) May 24, 1989.

Abstract of EP 282474 (Salzbrunn et al.) Sep. 14, 1988.

Abstract of SU 562573 (Fenikosva et al.) Sep. 21, 1977.

Abstract of JP 63–139249 (Sheseido Co. LTD) Jun. 11, 1988.

Abstract of EP 143412 (Boehringer Mannheim GmbH) Jun. 5, 1985.

Abstract of Buechele et al. (HRC CC, J. High Resolut. Chromatogr. Commun. (1979), 2(9), 585; Fluorimetric Determination of Sugars on HPTLC Plates) 1979 month not available.

A.P. Corfield, et al. "A Micromethod for the Quantitation of Sialoglycoconjugate Immobilization on Insoluble Supports: Its Use in the Preparation of Supports with Varying Ligand Concentration," *Analytical Biochemistry*, vol. 1, No. 2, Dec. 1979.

*Primary Examiner*—Kathryn L. Gorgos
*Assistant Examiner*—Alex Noguerola
*Attorney, Agent, or Firm*—Oliff & Berridge

[57] ABSTRACT

An immobilized complex of one or more labeled carbohydrates wherein the labeled carbohydrates have been derivatized in a substantially hydrophobic solvent system and components other then the complex have been removed by washing with a hydrophobic solvent.

10 Claims, No Drawings

LABELLED SUGARS IMMOBILIZED ON A SOLID SUPPORT

This is a rational stage application of PCT/GB94/01115 filed May 20, 1994.

FIELD OF THE INVENTION

This invention relates to labelled sugars, that can be used in carbohydrate analysis, and to their preparation.

BACKGROUND OF THE INVENTION

For the purposes of carbohydrate analysis, it is known to label oligosaccharides and other carbohydrates with detectable labels. Radio-active labels are widely used, but many prefer to use non-radio-active materials. Various chemical labels have been proposed, e.g. providing fluorescence. Particular fluorescent labels and their use, involving analysis of labelled sugars by differential migration on electrophoresis, are described in WO-A-9428423.

Labelling is generally performed by reaction of the carbohydrate and the labelling reagent in a homogeneous solution. The resultant labelled carbohydrate is then separated.

Immobilised reaction systems are well known. For example, it has been proposed to complex labelling reagents on CELITE. Covalent carbohydrate-support conjugates are also known.

SUMMARY OF THE INVENTION

According to the present invention, a labelled carbohydrate, e.g. monosaccharide or higher oligomer, is provided in the form of an immobilised complex. This is based on the discovery that there are suitable matrix materials which will bind sugars sufficiently, to allow the labelling reaction to proceed and then removal of substantially all contaminants from the immobilised complex of the labelled carbohydrate. This procedure avoids the additional steps associated with the prior art, i.e. "clean-up" steps that are necessary in order to provide the low background required for high sensitivity analysis, especially for capillary electrophoresis. Further, the approach adopted by the present invention reduces transfer and handling steps which can cause loss of sample.

DESCRIPTION OF THE INVENTION

The present invention takes advantage of the fact that sugars are hydrophilic molecules. They are labelled on the surface of a solid matrix such as glass (which is also hydrophilic), in a substantially hydrophobic solvent system. Excess labelling reagent may then be removed by washing the matrix with a hydrophobic solvent such as butanol, leaving the hydrophilic labelled sugars on the matrix surface. The technique therefore relies upon the labelling reagent having some hydrophobic character (which tends to be true for the majority of fluorescent and UV-absorptive labels).

Suitable matrices bind sugars sufficiently to allow the contaminants, i.e. including the reactants used in derivatisation, to be washed away without losing significant amounts of sugar in the washing process. A suitable solid phase matrix is controlled-pore glass (CPG).

In general terms, a conventional derivatisation reagent can be used. Examples are aminomethylfluorescein and 2-aminobenzoic acid (anthranilic acid); see WO-A-9428423, cited above, which discloses 2-aminobenzamide and analogues as labels, and references therein. It is added to the matrix, and derivatisation is allowed to proceed under appropriate conditions, e.g. reductive amination, given the materials involved. Clearly, reagents and conditions should be chosen so that the desired complex is formed, and the contaminants can be washed from it. Suitable materials for the washing step, such as butanol, can also be chosen from among those that are known.

Following derivatisation, sugar components remain bound to the solid phase, and then excess reagents and by-products may be washed away. The labelled sugars may then be eluted from the complex, substantially free of contamination. Again, a suitable eluant, such as water, may be readily selected by the skilled man. In consequence, the desired labelled carbohydrate is obtained in a satisfactory manner, and not in solution until so required.

The following Examples illustrate the invention. Examples 1 and 2 are in the nature of protocols.

EXAMPLE 1

1. Sample (consisting of an equimolar mixture of sugars, e.g. monosaccharides), dried into small tube which contains a small quantity of solid matrix (controlled pore glass).

2. Solution of labelling reagent (aminomethylfluorescein) added and dried onto glass matrix with sample.

3. Hydrophobic reaction solvent (butanol) added and reaction incubated for 1 hour.

4. Reductant added (also in substantially hydrophobic solvent) and reaction incubated for further two hours.

5. Reaction clean-up achieved by repeated washing with large volumes of hydrophobic butanol, which removes a considerable amount of the excess fluorescein label whilst labelled sugars remain attached to the matrix.

EXAMPLE 2 vial A—5-aminomethyl fluorescein-HCl (150 µg)

vial B—Borane-dimethylamine complex (60 mg/ml) in butanol/ethanol/water (4:1:1 v/v)

vial C—Standard monosaccharide mixture containing 1.12 nmoles each of glucose, mannose, galactose, fucose, N-acetylglucosamine.

vial D—Internal monosaccharide standard: 5.85 nmoles D-rhamnose.

vial E—Reaction vessel containing 0.5–1.0 mg adsorption matrix (controlled pore glass).

1. Dissolve contents of vial C in 50 µl water (HPLC grade) and transfer 10 µl to one or more reaction vessels (vial E) as desired. Dry using a centrifugal vacuum evaporator (c.v.e.)

2. Add 120 µl water (HPLC grade) to vial D and add 10 µl of this solution to each reaction vessel.

3. Take each reaction vessel to dryness (c.v.e.).

4. Prepare a 1 mg ml solution of dye by adding 150 µl methanol (HPLC grade) to vial A and vortex-mixing for a few seconds. Add 10 µl to each reaction vessel. Take to dryness (c.v.e.).

5. Add 3 µl n-butanol to each vessel, centrifuge briefly to bring all the butanol to the bottom of the vessel. Replace cap, and incubate at 60° C. for 60 minutes.

6. Vortex reductant solution for a few seconds and add 2 µl of solution to each reaction vessel. Replace caps and incubate reaction vessels at 60° C. for a further 120 minutes.

7. Remove reaction vessels from heat and add 200 μl n-butanol to each vessel. Recap the vessels and suspend the adsorption matrix by inverting and flicking the bottom of the vessel. Hold the vessel in the inverted position for 5–10 seconds, centrifuge briefly and discard the solvent phase using pipette tips. Repeat a further two times, and then dry (c.v.e.).

8. Add HPLC grade water (50–200 μl) to each vessel. Suspend the adsorption matrix as above (step 7), vortex, centrifuge and transfer the aqueous phase (or a determined aliquot thereof) to a CZE injection vial.

EXAMPLE 3

The protocols of Examples 1 and 2 were developed for the labelling of monosaccharides with aminomethylfluorescein for CZE analysis. In a particular run, in 200 mM borate/NaOH pH 8.5 at 27 kV, for 40 min, a CZE trace obtained from mixture of monosaccharides showed rhamnose, glucose, mannose, GlcNAc, fucose and galactose peaks at 26, c. 27.5, c. 28, 29, 30 and 31 min, with relative absorbences (peak heights) of approx. 5:9:6:2:4:9. A larger peak (20.5 min) indicated that not all reagent had been removed. Nevertheless, the process had removed a substantial part of it, and had thus reduced a number of reagent-derived peaks which would otherwise interfere with the sample peaks, to an insignificant level. The technique would be expected to work better with oligosaccharides than with monosaccharides.

EXAMPLE 4

A small aliquot (10 μl) of solution containing 1 nanogram/μl of rhamnose in water was added to a small microcentrifuge tube previously loaded with 1–2 mg of CPG (CPG Inc. Fairfield, N.J., U.S.A), and the solvent removed by vacuum centrifugation. Reductive amination was performed using 5-aminomethylfluorescein (Molecular Probes, Oregon, U.S.A) and dimethylaminoborane (Aldrich Chem. Co. Dorset, U.K) by first adding 2 μl of a solution of the dye (10 mg/ml) in DMSO, incubating for 30 minutes at 37° C., and then adding 2 μl of DMA-borane at 60 mg/ml in DMSO. After incubating at 37° C. for 2–3 hours, the DMSO was removed by evaporation, and the glass-bound product washed to remove reagents and by-products with three times 100 μl of n-butanol. Product was eluted with 200 μl of pure water, and analysed by capillary electrophoresis.

What is claimed is:

1. A process for preparing a labeled carbohydrate of at least one carbohydrate immobilized on a solid hydrophobic support, said process comprising:

applying at least one carbohydrate to the support, to immobilize said at least one carbohydrate;

subjecting, in a substantially hydrophobic solvent system, said at least one immobilized carbohydrate to reaction with a labelling reagent under derivitization conditions to form a labeled carbohydrate; and removing components, other than the labled carbohydrate, by washing with a hydrophobic solvent.

2. The process according to claim 1, wherein the solid support is a controlled-pore glass.

3. The process according to claim 1, wherein the labelling reagent is hydrophobic and fluorescent.

4. The process according to claim 1, wherein the complex comprises a plurality of immobilized oligosaccharides.

5. A process for analyzing at least one carbohydrate, which comprises the process according to claim 4 and further comprises subjecting the at least one eluted carbohydrate to electrophoresis.

6. The process according to claim 1, further comprising eluting the at least one labelled carbohydrate from the support.

7. The process according to claim 6, wherein the eluting step comprises using water.

8. A process for analyzing at least one carbohydrate comprising:

immobilizing said at least one carbohydrate on a hydrophilic support;

subjecting said at least one immobilized carbohydrate in a substantially hydrophobic solvent system to reaction with a labelling reagent to form a labeled carbohydrate;

removing components, other than the labeled carbohydrate, with a hydrophobic solvent; and eluting said at least one labelled carbohydrate with a hydrophilic solvent.

9. The process according to claim 8, further comprising subjecting the at least one eluted carbohydrate to electrophoresis.

10. The process according to claim 8, wherein the hydrophilic solvent is water.

* * * * *